(12) United States Patent
Leung et al.

(10) Patent No.: US 9,364,469 B1
(45) Date of Patent: Jun. 14, 2016

(54) IDENTIFICATION OF A NEW AMPK ACTIVATOR FOR TREATMENT OF LUNG CANCER

(71) Applicant: Macau University of Science and Technology, Macau (CN)

(72) Inventors: Lai-Han Leung, Macau (CN); Xiao-Jun Yao, Macau (CN); Kam Wai Wong, Macau (CN); Liang Liu, Macau (CN); Xi Chen, Macau (CN)

(73) Assignee: Macau University of Science and Technology, Macau (CN)

( * ) Notice: Subject to any disclaimer, the term of this patent is extended or adjusted under 35 U.S.C. 154(b) by 0 days.

(21) Appl. No.: 14/925,996

(22) Filed: Oct. 29, 2015

Related U.S. Application Data

(60) Provisional application No. 62/210,445, filed on Aug. 26, 2015.

(51) Int. Cl.
*A61K 31/4439* (2006.01)

(52) U.S. Cl.
CPC .................. *A61K 31/4439* (2013.01)

(58) Field of Classification Search
None
See application file for complete search history.

(56) References Cited

U.S. PATENT DOCUMENTS

| | | | |
|---|---|---|---|
| 2006/0235046 A1* | 10/2006 | Zacharchuk | A61K 31/47 514/313 |
| 2010/0087482 A1* | 4/2010 | Haber | A61K 38/17 514/313 |
| 2014/0371254 A1* | 12/2014 | Leung | A61K 31/4741 514/279 |

OTHER PUBLICATIONS

Engelman et al., Cancer Research (2007), 67(24), pp. 11924-11932.*
American Cancer Society. Cancer Facts & Figures 2015. Atlanta: American Cancer Society; 2015.
Hirsch, F.R. et al., Epidermal growth factor receptor in non-small-cell lung carcinomas: correlation between gene copy number and protein expression and impact on prognosis. Journal of Clinical Oncology, vol. 21, No. 20 Oct. 15, 2003: pp. 3798-3807.
Tam, I.Y.S. et al., Double EGFR mutants containing rare EGFR mutant types show reduced in vitro response to gefitinib compared with common activating missense mutations. Mol Cancer Ther 2009, 8(8): 2142-2151.
Leung, E. L. et al., SRC promotes survival and invasion of lung cancers with epidermal growth factor receptor abnormalities and is a potential candidate for molecular-targeted therapy. Mol Cancer Res 2009, 7(6): 923-932.
Pao, W. & Girard, N. New driver mutations in non-small-cell lung cancer. Lancet Oncol 2011, 12: 175-180.
Ji, H. et al. LKB1 modulates lung cancer differentiation and metastasis. Nature 2007, 448: 807-810.
Ding, L. et al. Somatic mutations affect key pathways in lung adenocarcinoma. Nature 2008, 455(7216): 1069-1075.
Tanaka, T. et al. Frequency of and variables associated with the EGFR mutation and its subtypes. Int. J. Cancer 2010, 126(3): 651-655.
Niu, X., Fan, T. Li, W. Xing, W & Huang, H. The anti-inflammatory effects of sanguinarine and its modulation of inflammatory mediators from peritoneal macrophages. Eur. J. Pharmacol 2012, 689(1-3): 262-269.
Seyfried, T. N., Flores, R., Poff, A. M. & D'Agostino, D. P. Cancer as a metabolic disease: implications for novel therapeutics. Carcinogenesis 2014, 35(3): 515-527.
Klubo-Gwiezdzinska, J. et al. Metformin inhibits growth and decreases resistance to anoikis in medullary thyroid cancer cells. Endocr Relat Cancer 2012, 19: 447-456.
Tulipano, G. et al. Effects of AMPK activation and combined treatment with AMPK activators and somatostatin on hormone secretion and cell growth in cultured GH-secreting pituitary tumor cells. Mol Cell Endocrinol 2013, 365: 197-206.
Mukherjee, P. et al. Differential effects of energy stress on AMPK phosphorylation and apoptosis in experimental brain tumor and normal brain. Mol Cancer 2008, 7: 37.
Goransson, O. et al. Mechanism of action of A-769662, a valuable tool for activation of AMP-activated protein kinase. J Biol Chem 2007, 282(45): 32549-32560.
Watson, J. D. Type 2 diabetes as a redox disease. Lancet 2014, 383: 841-843.
Liang, J. & Mills, G. B. AMPK: a contextual oncogene or tumor suppressor? Cancer Res. 2013, 73(10): 2929-2935.
Zhan, Y. et al. Control of cell growth and survival by enzymes of the fatty acid synthesis pathway in HCT-116 colon Cancer cells. Clin Cancer Res 2008, 14(18): 5735-5742.
Hawley, S. A. et al. Characterization of the AMP-activated protein kinase kinase from rat liver and identification of threonine 172 as the major site at which it phosphorylates AMP-activated protein kinase. J Biol Chem 1996, 271(44): 27879-27887.
Hardie, D. G. & Pan, D. A. Regulation of fatty acid synthesis and oxidation by the AMP-activated protein kinase. Biochem Soc Trans 2002, 30(6): 1064-1070.
Longnus, S. L, Wambolt, R. B., Parsons, H. L., Brownsey, R. W. & Allard, M. F. 5-Aminoimidazole-4-carboxamide 1-beta-D-ribofuranoside (AICAR) stimulates myocardial glycogenolysis by allosteric mechanisms. Am J Physiol Regul Integr Comp Physiol 2003, 284: R936-944.

* cited by examiner

*Primary Examiner* — Brian J Davis
(74) *Attorney, Agent, or Firm* — Eagle IP Limited; Jacqueline C. Lui

(57) ABSTRACT

The present invention discloses a method of treating gefitinib-resistant non-small-cell lung cancer, comprising administering an effective amount of D561-0775. A pharmaceutical composition comprising D561-0775 admixed with a pharmaceutical carrier for treating Gefitinib-resistant non-small-cell lung cancer is also disclosed therein.

6 Claims, 7 Drawing Sheets
(4 of 7 Drawing Sheet(s) Filed in Color)

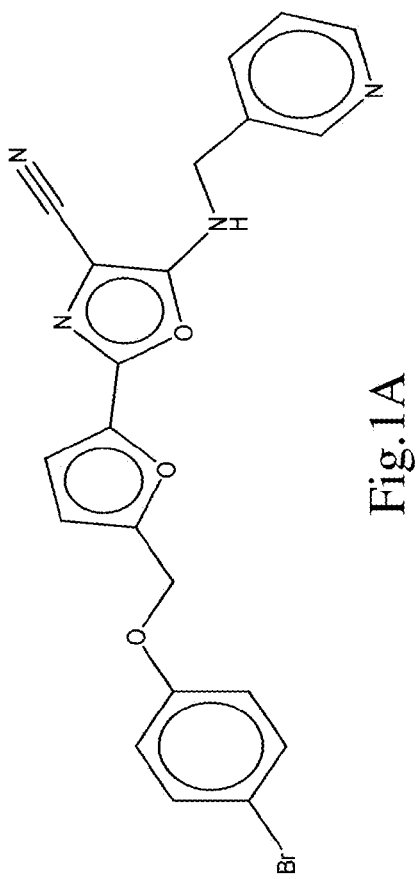
Fig.1A
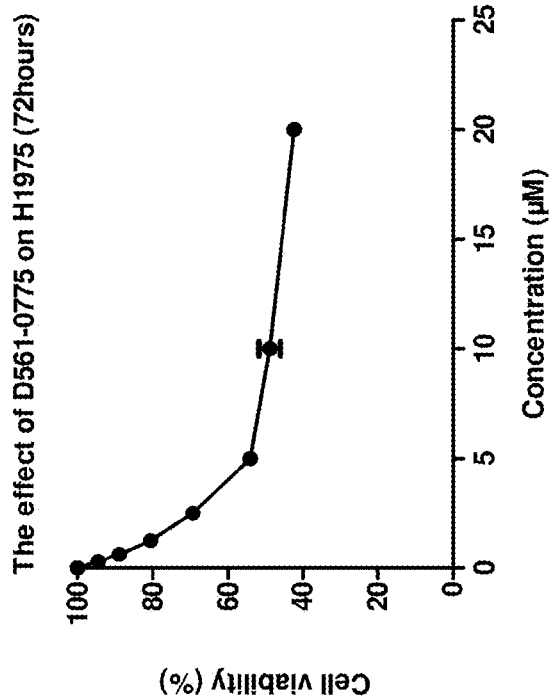
Fig.1B
| Cell line | IC50 (μM) |
|---|---|
| H1975 | 9.59±1.73 |
Fig.1C

IDENTIFICATION OF A NEW AMPK ACTIVATOR FOR TREATMENT OF LUNG CANCER

CROSS-REFERENCE TO RELATED APPLICATION

This application claims benefit under 35 U.S.C. §119(e) of U.S. Provisional Application having Ser. No. 62/210,445 filed 26 Aug. 2015, which is hereby incorporated by reference herein in its entirety.

FIELD OF INVENTION

This invention relates to a novel treatment for treating non-small-cell lung cancer, in particular, a novel treatment involving the use of an AMPK activator.

BACKGROUND OF INVENTION

Lung cancer is the major cause of human death in the world. Epidermal growth factor receptor (EGFR) is highly expressed in more than 60% of non-small cell lung cancer (NSCLC) patients. With the development of cancer therapeutic, more and more specific genetic mutations have been identified in NSCLC, for examples, EGFR, anaplastic lymphoma kinase (ALK), KRAS, ROS, and LKB1.

These were taken as molecular targets for individual comprehensive therapy for NSCLC patients. About 85% of EGFR mutations identified from patients are in-frame deletions in exon19 and the L858R point substitution in exon 21 of EGFR, which are biomarkers for good response to EGFR tyrosine kinase inhibitors (TKIs). Although it is an outstanding therapy for most patients with EGFR mutation, another new additional EGFR mutation such as T790M were identified, which eventually led to TKI resistance after one year. Therefore, it is urgently needed to discover more effective agents as candidate drugs for TKIs-resistant NSCLC patients.

SUMMARY OF INVENTION

In the light of the foregoing background, it is an object of the present invention to provide an alternate treating method.

Accordingly, the present invention, in one aspect, is a method of treating gefitinib-resistant cancer, comprising administering an effective amount of D561-0775.

In an exemplary embodiment of the present invention, the gefitinib-resistant cancer is non-small-cell lung cancer. In a further embodiment, the gefitinib-resistant non-small-cell lung cancer has double mutation of L858R and T790M.

According to another aspect of the present invention, it provides a pharmaceutical composition comprising D561-0775 admixed with a pharmaceutical carrier for treating gefitinib-resistant cancer.

In an exemplary embodiment of the present invention, the gefitinib-resistant is non-small-cell lung cancer. In a further embodiment, the gefitinib-resistant non-small-cell lung cancer has double mutation of L858R and T790M.

BRIEF DESCRIPTION OF FIGURES

The patent or application file contains at least one drawing executed in color. Copies of this patent or patent application publication with color drawing(s) will be provided by the Office upon request and payment of the necessary fee.

FIG. 1A shows the chemical structure of D561-0775. FIG. 1B shows the dose response curve of D561-0775 in H1975 cells. The IC50 thereof is shown in FIG. 1C.

DETAILED DESCRIPTION OF THE PREFERRED EMBODIMENTS

Figure 2A:
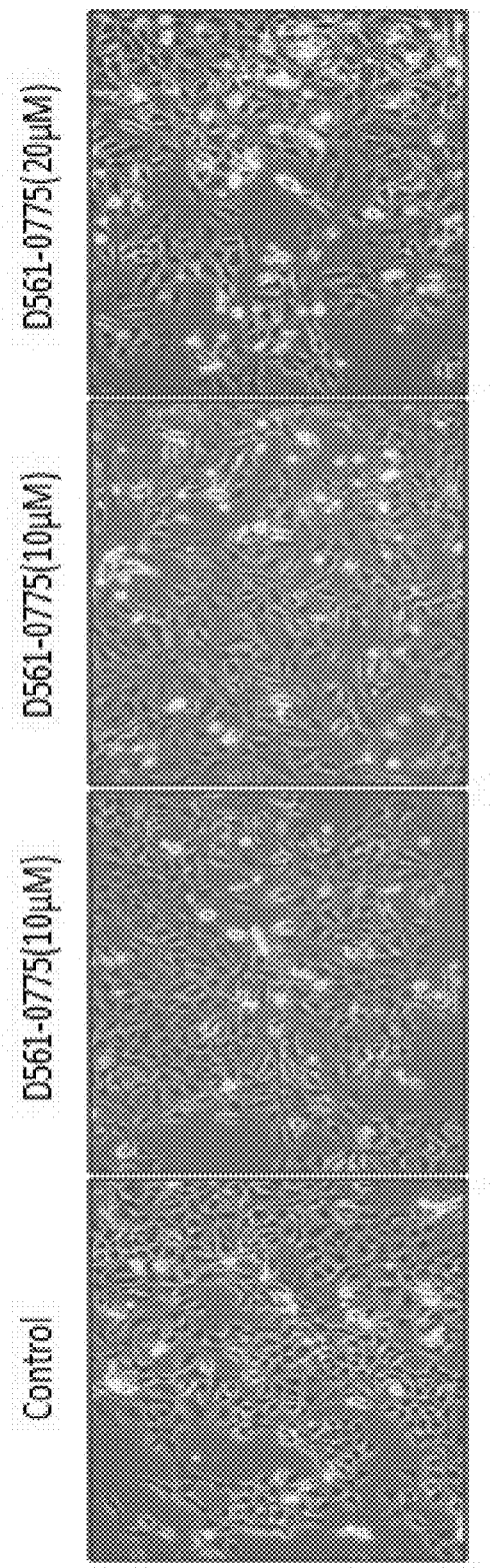
FIGS. 2A, 2B and 2C show that D561-0775 induced apoptosis in H1975 cells.

As used herein and in the claims, "comprising" means including the following elements but not excluding others.

Nowadays, many researchers considered cancer as metabolic diseases. 5'-adenosine menophosphate-activated protein kinase (AMPK) is a vital enzyme in regulating energy homeostasis, which is considered as one of the master control regulators of cellular and organism metabolism. Many studies confirmed that AMPK activators can inhibit the proliferation and migration of tumor cells.

As a metabolism rate-limiting enzyme, AMPK is the potential target for treatment of NSCLC. AMPK could be activated by activation of upstream LKB1/CaMKKβ or low energy status to switch on ATP producing catabolic pathways and switch off ATP-consuming anabolic pathways to restore cellular energy homeostasis. It could also be allosterically activated by AMPK direct activator, such as A769662. Activated AMPK adjusts its downstream channels through the cascade (e.g. ACC, mTOR, TSC1/2) to regulate energy metabolism. Therefore, AMPK is a potential new lung cancer target for drug research and development. In fact, several AMPK activators have already been approved in clinical trials (http://clinicaltrials.gov, IDs NCT01210911, NCT01266486).

In this invention, the inventors have applied high throughput screening of new AMPK activator from a small-molecule library using molecular docking technique. The inventors then used kinase-based and cell-based assays to detect the AMPK activation of several compounds on a gefitinib-resistant NSCLC cell line with EGFR double mutation (H1975$^{L858R+T790M}$). The result showed that D561-0775 is a potent AMPK activator. It can directly activate AMPK activity through phosphorylation of AMPK at Thr172 site, and it can also induce apoptosis in H1975 cells via regulation of lipogenesis. This compound has the potential to be developed as new anti-cancer drug for lung cancer treatment.

Material and Methods

1. Cell Culture and Reagents

H1975 was purchased from ATCC (American type culture collection) and was cultivated with RPMI 1640 medium supplement with 10% fetal bovine serum (Gibco, Big Cabin, Oklahoma, Me., USA), 100 U/mL, penicillin and 100 μg/mL and streptomycin (Gibco, Big Cabin, Oklahoma, Me., USA). The cells were cultured in incubator with 5% $CO_2$ at 37° C.

D561-0775 was purchased from Top Science Co. Ltd (Shanghai, China). The primary anti-bodies of GAPDH, total/phosphor-AMPK, total/phosphor-ACC were purchased from Cell Signaling Technology (Danvers, Mass., USA). Fluorescein-conjugated anti-rabbit as secondary anti-body was purchased from Odyssey (Belfast, Me., USA).

2. MTT Cytotoxicity Assay

Cells were seeded in a 96-well microplate with 5000 cells/well confluence, and put into the incubator overnight for cell adhesion. Different concentrations of the drug D561-0775 were added with Dimethyl sulfoxide (DMSO) as vehicle control. The microplates were incubated for another 72 hours. The whole experiment was repeated in triplicate. 10 μL of MTT (5 mg/mL) solution was added to each well. The plate was placed back into the incubator for 4 hours. After that, 100 μL of resolved solution (10% SDS and 0.1 mM HCL) was added to each well. Before dissolving the formazan crystals, the microplate was put back into the incubator for another 4 hours. The absorbance of the plate was measured at 570 nm with reference at 650 nm by a microplate reader (Tecan, Morrisville, N.C., USA). Cell viability was calculated by percentages of the absorbance of the treatment group divided by the absorbance of untreated group. At least three independent experiments were performed for data analysis and presentation.

3. Apoptosis Assay

H1975 cells ($1 \times 10^5$ cells/well) were seeded in a 6-well plate for 24 hours, and treated with the indicated concentrations of D561-0775 for an additional 48 hours at 37° C. After 48 hours, the cells were washed by ice-cold 1×PBS once and harvested by trypsination. Then cells were centrifuged, collected and re-suspended in ice-cold 1×PBS. After removing the supernatants, cell pellets were re-suspended in 100 μL 1× Annexin-binding buffer. The cells were then double-stained with Annexin-V FITC and PI (100 μg/mL) of 2 μL respectively for 15 min at room temperature in dark. After that, 300 μL 1× Annexin-binding buffer was added. Apoptotic cells were quantitatively counted by a BD Aria III Flow Cytometer (BD Biosciences, San Jose, Calif., USA)

4. Western Blot Analysis

After incubating H1975 cells with D561-0775 for 24 hours, H1975 cells were harvested and washed with cold 1×PBS. Then, cells were lysed with ice-cold RIPA lysis buffer with protease and phosphatase inhibitors added to extract the cell protein extraction. The supernatants were collected by centrifugation at 12,000 g, for 5 minutes. The quantitation of total protein extraction was measured by Bio-Rad DCTM protein assay kit (Bio-Rad, Philadelphia, Pa., USA). Then 30 μg of protein was loaded and electrophoretically separated on 8% SDS-PAGE gel and then transferred to Nitrocellulose (NC) membrane. Membranes were blocked with 5% non-fat milk and PBS containing 0.1% Tween-20 (TBST) for 1 hour at room temperature. After 1 hour, membranes were incubated with primary anti-bodies (1:1000 dilution) against GAPDH, total/phosphor-ACC, total-AMPK, and (1:500 dilution) against phosphor-AMPK, at 4° C. with gently shaking overnight. Membranes were washed with TBST for 3 times (5 minutes/time), and incubated with secondary fluorescent antibody (1:10000 dilutions) for 1 hour at room temperature. After rewashing the membranes with TBST for 3 times (15 minutes/time), the stripes were visualized by LI-COR Odessy scanner (Belfast, Me., USA).

5. AMPK Enzyme Activity Assay

The CycLex AMPK Kinase Assay Kit (CycLex Co., Ltd., Nagano, Japan) was used to detect the activation of AMPK by D561-0775. AMP was used as positive control, compound c was used as AMPK inhibitor, and AMPK kinase was used for representing the basal level.

6. Molecular Docking Study on the Interaction Between D561-0775 and AMPK.

Molecular docking calculation is performed to study the binding mode of D561-0775 to the adenosine 5'-monophosphate (AMP)-activated protein kinase (AMPK) using Glide programming Schrodinger software (Schrodinger, Inc., New York, N.Y., 2009). The structure of D561-0775 was processed by the LigPrep based on OPLS-2005 force field. The 3D structure of AMPK for molecular docking was retrieved from the Protein Data Bank (PDB ID: 4CFE) and was processed by the Protein Preparation Wizard module. D561-0775 was docked into the binding site of the AMPK with the standard precision (SP) scoring mode. The docking grid box was defined by centering on the compound 991 in the complex of AMPK and ligand (PDB ID: 4CFE).

7. Statistical Analysis

All the data was presented as mean±SD of 3 individual experiments. Differences were analyzed by one-way ANOVA using Graph Prism 5.

Results

1. Cytotoxicity Effect of D561-0775 on NSCLC Cells

The chemical structure of D561-0775 and dose response curve were shown in FIG. 1A and FIG. 1B respectively. MTT assay showed that D561-0775 can inhibit cell proliferation on H1975 cells. The IC50 value of D561-0775 is 9.59±1.73 μM after 72 h treatment.

Figure 2B:
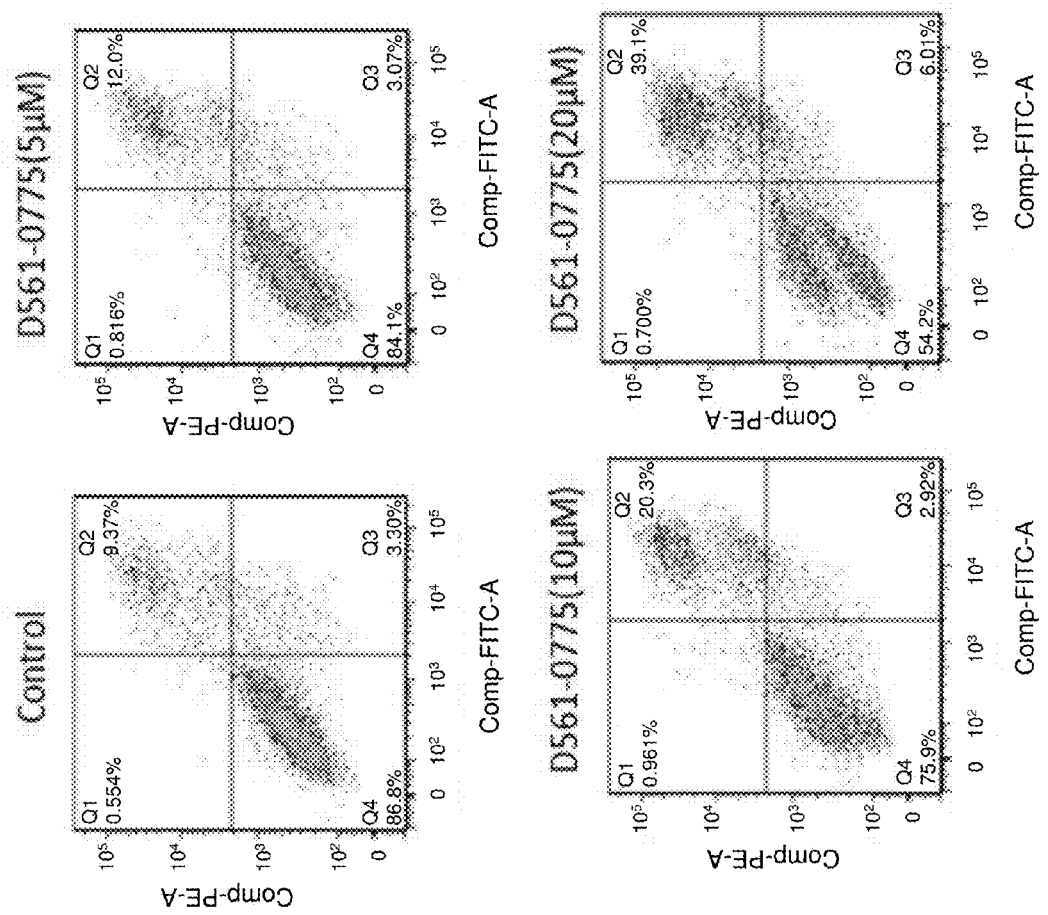
Figure 2C:
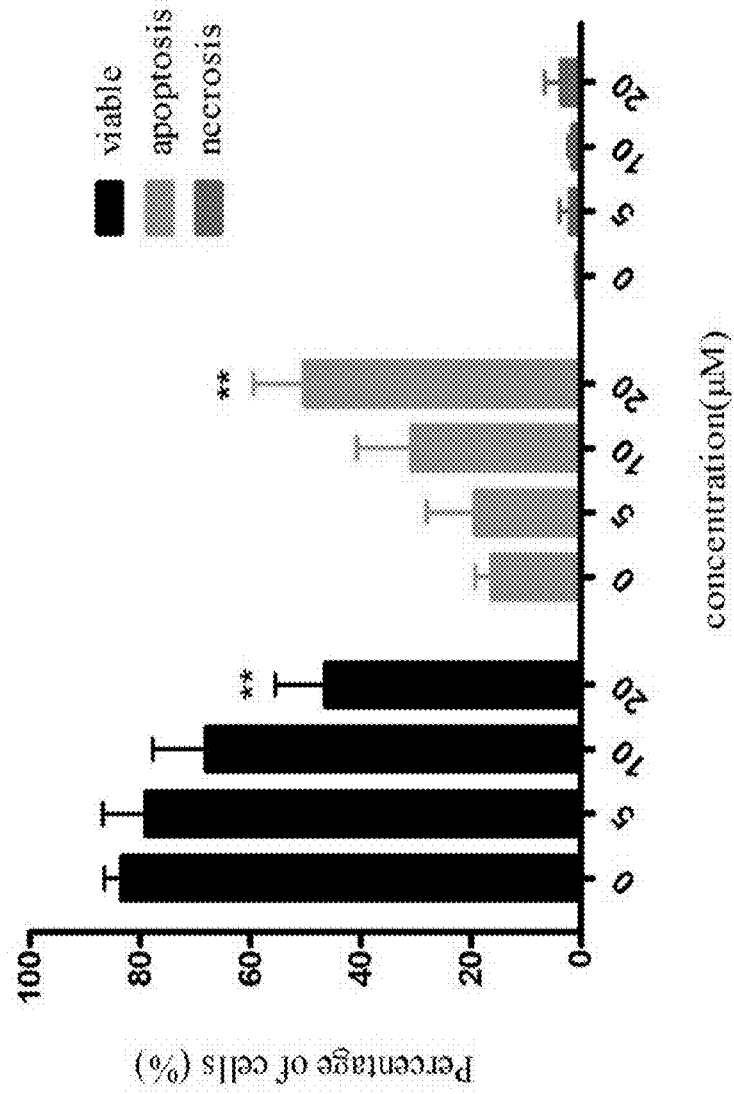

2. D561-9775 Significantly Induced Apoptosis in H1975 Cells as Examined by Quantitative Annexin V/PI Flow Cytometry Analysis By morphology observation, after treating H1975 cells with D561-0775 for 48 h, the treated cells floated and rounded-up starting at 20 μM as shown in FIG. 2A, which is an indication of apoptosis. Then by using quantitative apoptosis measurement method, flow cytometry analysis showed that D561-0775 induced significant level of apoptosis in a dose-dependent manner as shown in FIG. 2B. On comparing with the control group, D561-0775 showed significant higher percentage of apoptotic cells and lower percentage of viable cells in the 20 μM treatment group (**$p<0.01$, n=3) as shown in FIG. 2C.

3. D561-0775 Dose-Dependently Increases AMPK Phosphorylation as Well as Fatty Acid Oxidation.

Previous studies demonstrated that phosphorylation AMPK signal can activate acetyl-CoA carboxylase (ACC), while cancer cell proliferation requires lipids for cell membrane synthesis.

As an AMPK downstream component, ACC is an important regulator of fatty acid oxidation. When AMPK was activated by phosphorylation on Thr172 site, ACC was phosphorylated to increase fatty acid oxidation.

Figure 3:
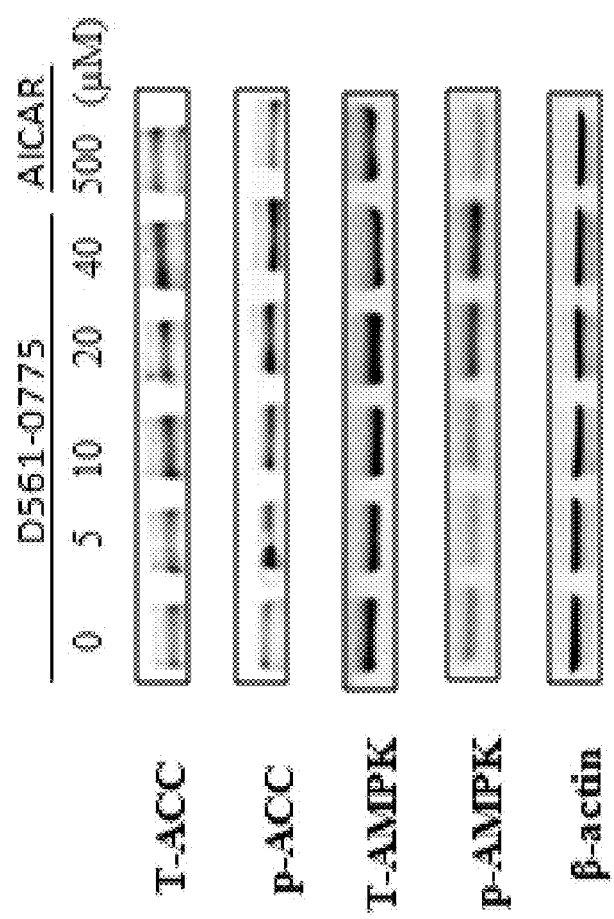
FIG. 3 shows the western blot analysis of D561-0775 activated phosphorylation of both AMPK and ACC. T-AMPK/p-AMPK and T-ACC/p-ACC represent total/phosphor-AMPK and total/phosphor-ACC respectively.

Western blot analysis as shown in FIG. 3 illustrated that D561-0775 activated phosphorylation of both AMPK and ACC in a dose-dependent manner, indicating that the anticancer efficacy is mediated by suppression of lipogenesis. β-actin was used a loading control while AICAR (5-Aminoimidazole-4-carboxamide ribonucleotide) was used a positive control because AICAR was previously reported to be an AMPK activator.

4. D561-0775 Directly Activates AMPK Kinase

Figure 4:
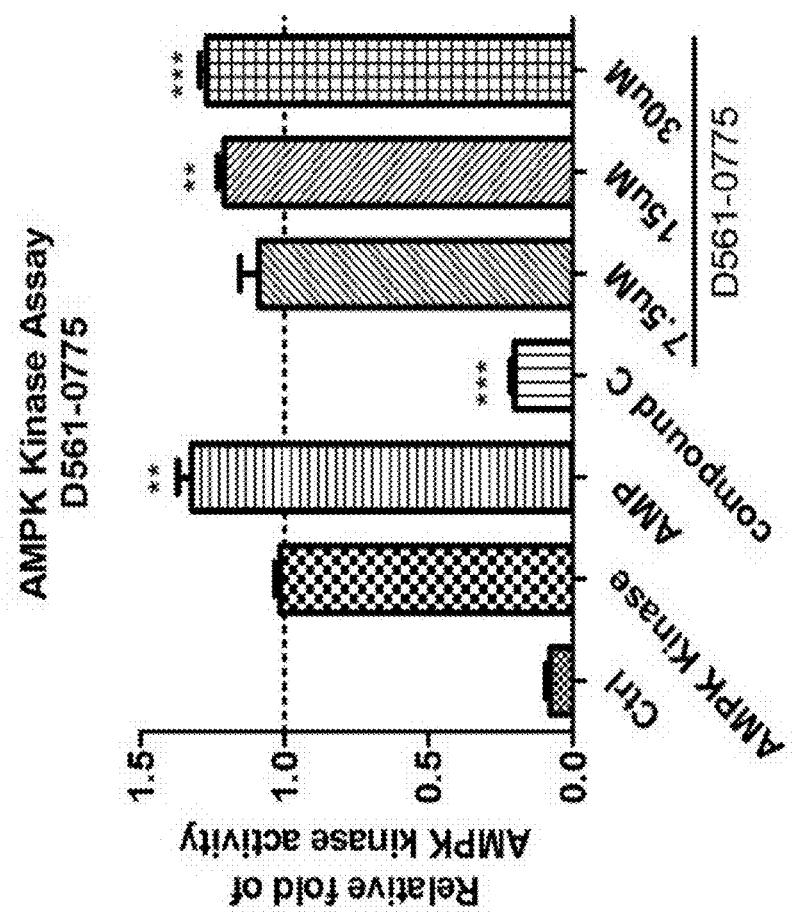
FIG. 4 shows the results of an AMPK kinase activity assay performed by treating H1975 cells with indicated concentration of D561-0775.

AMPK kinase activity assay was performed by treating H1975 cells with indicated concentrations of D561-0775. As shown in FIG. 4, AMPK kinase activity was enhanced in a dose-dependent manner (n=3,  $p<0.005$, *$p<0.001$). AMPK kinase was used to indicate the basal activity level, and all enzyme activities were presented as fold of the AMPK kinase alone group. Compound C, the AMPK inhibitor, was used as negative control. AMP was also used as positive control.

5. Computational Docking of D561-0775 with AMPK Model

Figure 5:
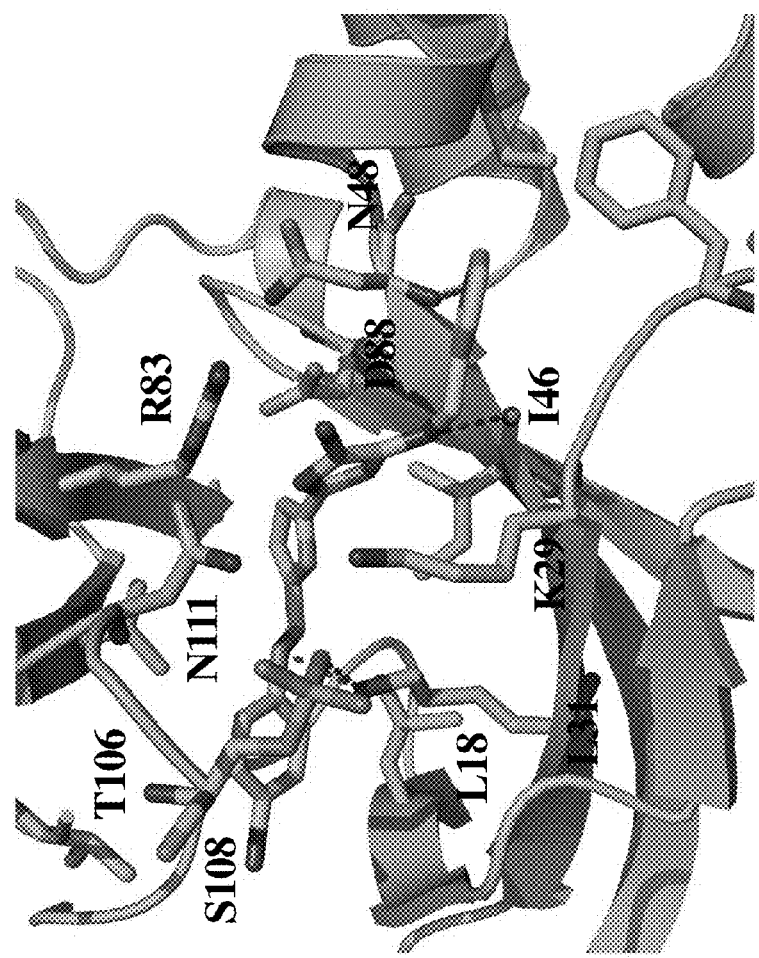
FIG. 5 shows the binding mode of D561-0775 docked into the active site of AMPK.

The binding mode of D561-0775 docked into the active site of AMPK was shown in FIG. 5. The interactions between AMPK and D561-0775 mainly consist of hydrophobic, polar and hydrogen bond interactions. The hydrophobic groups of D561-0775 form hydrophobic interactions with the side chain of L18, L31, I46 and T106. The polar groups of D561-0775 form polar interactions with the side chain of I46, L31, N48, R83, D88, S108 and N11. In addition, D561-0775 also form hydrogen bonds with the backbone of I46 and N48 and the side chain of L31.

Further, as illustrated in FIG. 5, the AMPK protein is represented as cartoon. AMPK and key residues around the binding pocket are shown as sticks. The hydrogen bond is labeled as red dashed lines.

CONCLUSION

In this invention, the inventors have identified a new AMPK activator D561-0775, which targets the metabolism switch-AMPK kinase, and shows potent anti-cancer activity in gefitinib-resistant NSCLC cell with EGFR double mutation (H1975). D561-0775 is also illustrated to directly activate AMPK kinase, induce apoptosis and phosphorylates downstream ACC in H1975 cells. In summary, this compound has great potential to be developed as new anti-cancer drug for gefitinib-resistant NSCLC patients by targeting AMPK kinase.

The exemplary embodiments of the present invention are thus fully described. Although the description referred to particular embodiments, it will be clear to one skilled in the art that the present invention may be practiced with variation of these specific details. Hence this invention should not be construed as limited to the embodiments set forth herein.

What is claimed is:

1. A method of treating gefitinib-resistant cancer, comprising administering an effective amount of D561-0775.
2. The method of claim 1 wherein said gefitinib-resistant cancer is non-small-cell lung cancer.
3. The method of claim 2 wherein said gefitinib-resistant non-small-cell lung cancer has double mutation of L858R and T790M.
4. A pharmaceutical composition comprising D561-0775 admixed with a pharmaceutical carrier for treating gefitinib-resistant cancer.
5. The pharmaceutical composition of claim 4 wherein said gefitinib-resistant cancer is non-small-cell lung cancer.
6. The pharmaceutical composition of claim 5 wherein said gefitinib-resistant non-small-cell lung cancer has double mutation of L858R and T790M.

* * * * *